United States Patent [19]

Bartmann et al.

[11] 4,182,773

[45] Jan. 8, 1980

[54] NOVEL PROSTAGLANDIN DERIVATIVES

[75] Inventors: Wilhelm Bartmann, Bad Soden am Taunus; Ulrich Lerch, Hofheim am Taunus; Hermann Teufel; Bernward Schölkens, both of Kelkheim; Gerhard Beck, Frankfurt am Main, all of Fed. Rep. of Germany

[73] Assignee: Hoechst Aktiengesellschaft, Frankfurt am Main, Fed. Rep. of Germany

[21] Appl. No.: 816,207

[22] Filed: Jul. 15, 1977

[30] Foreign Application Priority Data

Jul. 16, 1976 [DE] Fed. Rep. of Germany ....... 2632097
Jan. 21, 1977 [DE] Fed. Rep. of Germany ....... 2702370

[51] Int. Cl.$^2$ .................. C07C 177/00; A61K 31/19; A61K 31/215
[52] U.S. Cl. .................................. 424/305; 260/410; 560/121; 560/231; 562/503; 424/311; 424/317; 549/22; 549/39; 260/340.7; 260/340.9 P; 260/340.9 R
[58] Field of Search ............... 560/121, 231; 562/503; 260/410

[56] References Cited

U.S. PATENT DOCUMENTS 4,024,181 5/1977 Babej et al. ......................... 260/514

Primary Examiner—Robert Gerstl

Attorney, Agent, or Firm—Curtis, Morris & Safford

[57] ABSTRACT

What is disclosed are prostaglandin-analogous cyclopentane derivatives of the formula I

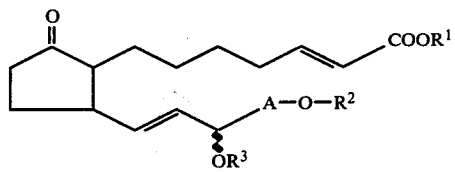

wherein
$R^1$ is hydrogen or a linear or branched, saturated or unsaturated aliphatic or cycloaliphatic radical having from 1 to 8 carbon atoms, or an araliphatic radical having from 7 to 9 carbon atoms, or a physiologically tolerable metal, $NH_4$ or substituted ammonium ion derived from a primary, secondary or tertiary amine;
$R^2$ is a linear or branched, saturated or unsaturated aliphatic hydrocarbon radical having from 1 to 8 carbon atoms;
$R^3$ is hydrogen or a $R^4CO$ group wherein $R^4$ is a hydrogen atom or a linear or branched alkyl group having up to 10 carbon atoms;
A is a saturated, linear or branched alkylene group having from 2 to 5 carbon atoms, and a process for the manufacture thereof.

2 Claims, No Drawings

NOVEL PROSTAGLANDIN DERIVATIVES

Prostaglandins are a group of fatty acids present in various tissues and organs of man and animal. The basic skeleton of the natural prostaglandins consists of 20 carbon atoms arranged in the form of a five-membered ring with two adjacent linear side chains.

The pharmacological effects of the prostaglandins are manifest in the fields of reproduction, blood pressure, gastroenterology, in the bronchial muscle tonus etc. The pharmacological properties of the natural prostaglandins are the subject of numerous synoptic papers, for example N. Andersen and P. W. Ramwell, Arch. Internal Med. 133, 30 (1974); R. L. Jones, Pathobiology Ann. 1972, 359; J. Pike, Scient. American 225, 94 (1971), or M. P. L. Caton, Progress in Med. Chem., vol. 8, ed. Butterworth, London, 1971.

The synthesis of analogs of prostanoic acids which do not occur in nature and in which the great number of pharmacological actions of the natural prostaglandins is differentiated is of increasing importance.

The present invention provides novel prostaglandin-analogous cyclopentane derivatives of the formula I

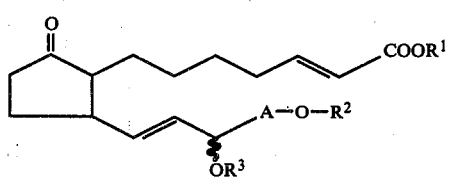

wherein
  $R^1$ is hydrogen or a linear or branched, saturated or unsaturated aliphatic or cycloaliphatic radical having from 1 to 8 carbon atoms, or an araliphatic radical having from 7 to 9 carbon atoms, or a physiologically tolerable metal, $NH_4$ or substituted ammonium ion derived from a primary, secondary or tertiary amine;
  $R^2$ is a linear or branched, saturated or unsaturated aliphatic hydrocarbon radical having from 1 to 8 carbon atoms;
  $R^3$ is hydrogen or a $R^4CO$ group wherein $R^4$ is a hydrogen atom or a linear or branched alkyl group having up to 10 carbon atoms;
  A is a saturated, linear or branched alkylene group having from 2 to 5 carbon atoms.

The present invention provides furthermore a process for the manufacture of the cyclopentane derivatives of formula I, which comprises (a) oxidizing an alcohol of the formula II

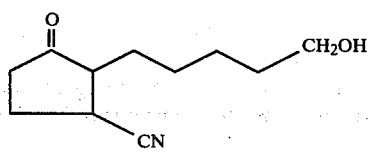

to form an aldehyde of the formula III

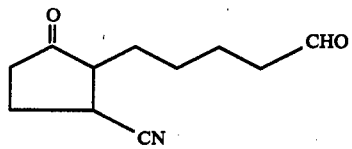

(b) converting the aldehyde of formula III with a dithiol of the formula IV

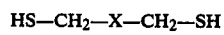

wherein X is a single bond, a $CH_2$ group or a

group, in the presence of acidic catalysts, to a dithioacetal of the formula V

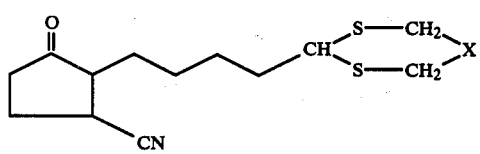

(c) reacting the dithioacetal of formula V with a diol of the formula VI

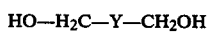

VI wherein Y is a single bond, a $CH_2$ group or a

group, in the presence of acidic catalysts, to form a ketal of the formula VII

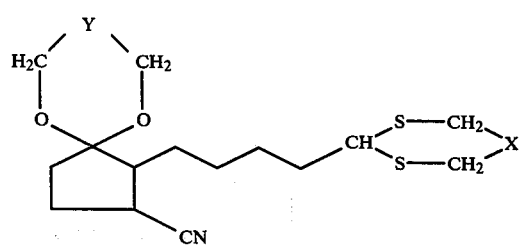

(d) reducing the nitrile of formula VII to an aldehyde of the formula VIII

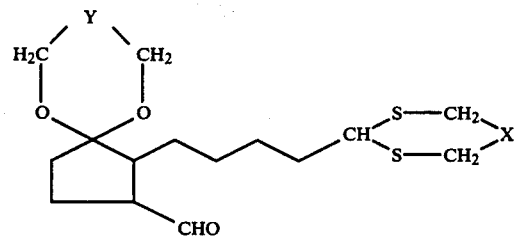

(e) reacting the aldehyde of formula VIII with a phosphonate of the formula IX

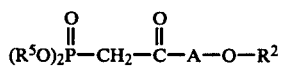

wherein A and $R^2$ are as defined for formula I, and $R^5$ is a linear or branched alkyl radical having from 1 to 4 carbon atoms, to form an unsaturated ketone of the formula X

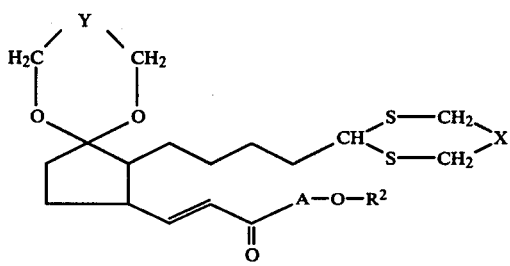

(f) reducing the unsaturated ketone of formula X to an alcohol of the formula XI

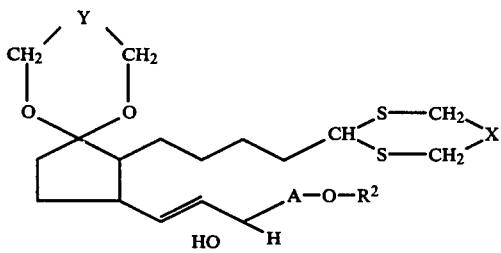

(g) splitting off carefully the thioacetal group of the compound of formula XI, thus forming an aldehyde of the formula XII

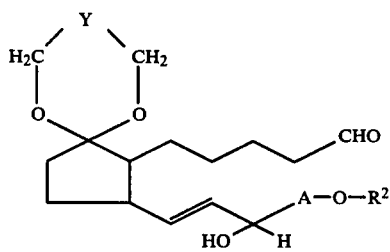

(h) reacting a compound of formula XII with an ylide of the formula XIII

   XIII wherein the radicals $R^6$ may be identical or different and each are linear alkyl having from 1 to 4 carbon atoms or phenyl, and $R^1$ is as defined for formula I, to form a compound of the formula XIV

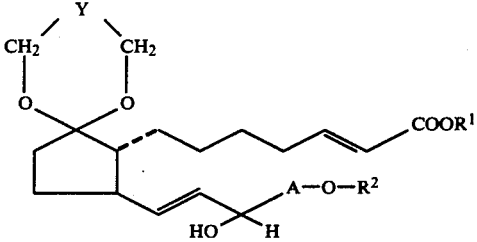

wherein $R^1$, $R^2$ and A are as defined for formula I; $R^1$ however not being hydrogen;

(i) removing the ketal protecting group of the compound of formula XIV by means of acidic solvolysis, thus obtaining a compound of formula I, wherein $R^3$ is hydrogen and $R^1$, $R^2$ and A are as defined for formula I, and optionally (j) converting the compound so obtained to a physiologically tolerable metal, $NH_4$ or substituted ammonium salt, and optionally (k) reacting the ester so obtained or the salt with an acylating agent to form a compound of the formula I

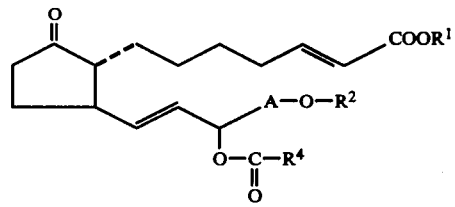

wherein $R^4$ is as defined for formula I, and optionally preparing therefrom the free acid wherein $R^1$ is H.

Preferred substituents are the following:

For $R^1$: hydrogen, a linear or branched alkyl radical having from 1 to 8 carbon atoms, a linear or branched alkenyl radical having from 2 to 4 carbon atoms, a cycloalkyl radical having from 5 to 7 carbon atoms, an aralkyl radical having 7 or 8 carbon atoms, or a physiologically tolerable metal, $NH_4$, or substituted ammonium ion derived from a primary, secondary or tertiary amine.

For $R^2$: a linear, branched, saturated or unsaturated aliphatic hydrocarbon radical having from 1 to 8 carbon atoms.

For $R^3$: hydrogen or a $R^4CO$ group, wherein $R^4$ is a hydrogen atom or a linear or branched alkyl group having up to 4 carbon atoms.

For A: a saturated, linear or branched alkylene group having from 2 to 5 carbon atoms.

The 2(5-hydroxypentyl)-3-oxo-cyclopentylnitrile of formula II used as starting material in the process of the invention may be prepared according to various processes. A method used in the process of the invention is the following:

A cyclopentane-2-one-carboxylic acid ethyl ester of the formula

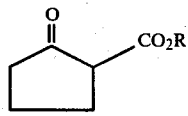

is reacted with 5-acetoxy-pentyl iodide of the formula

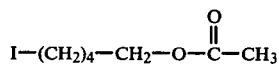

to form the 1-substituted cyclopentane-2-one-carboxylic acid ethyl ester of the formula XX

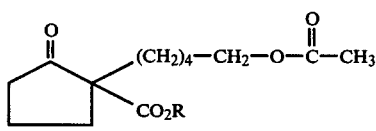

which is decarboxylated by means of glacial acetic acid/$H_2SO_4$ to form the compound XXI

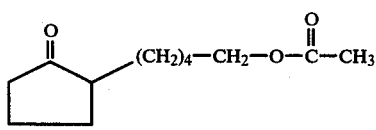

which is treated according to the process of German Offenlegungsschrift No. 2,430,700 in order to obtain the compound II via the compounds XXII and XXIII

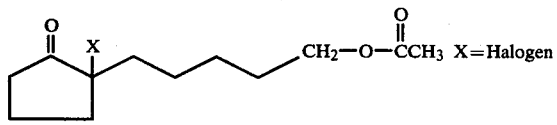

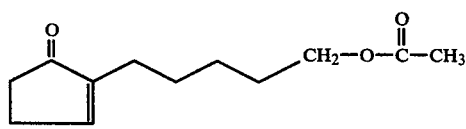

The process of the invention consists in oxidizing the alcohol of formula II to the aldehyde of formula III.

The oxidation of II to III is carried out with oxidation agents useful for the oxidation of aliphatic alcohols to aldehydes. Some of these methods are indicated for example in Houben-Weyl, Methoden der Organischen Chemie, Vol. 7/1, Stuttgart 1954, p. 159 sqq.

Further suitable oxidation agents are the complex formed of thioanisol and chlorine (J. Org. Chem. 38, 1233 (1973)), the chromium trioxide/pyridine complex (J. Org. Chem. 35, 4000 (1970) and J. Org. Chem. 26, 4814 (1961)), and dimethyl sulfoxide with different co-reactants (J. Amer. Chem. Soc. 87, 5661 (1965), 88, 1762 (1966), 89, 5505 (1967); Chem. Rev. 67, 247 (1967)).

A particularly preferred process is the oxidation with the complex formed of dimethyl sulfoxide and N-chlorosuccinimide, preferably according to the description in J. Amer. Chem. Soc. 94, 7586 (1972).

The aldehyde of formula III may then be purified by distillation or chromatography; however, it is advantageous to react it directly in crude form with dithiols of formula IV in inert solvents and in the presence of acidic catalysts to form the dithioacetals of formula V.

The selective protection of the aldehyde group of III before the keto function also present in III is obtained by operating with about stoichiometric amounts of dithiols of formula IV, the reaction being carried out at a temperature of from $-10°$ to $-30°$ C.

A preferred embodiment of the process of the invention is the following:

the crude aldehyde III is reacted with a small excess of a dithiol of formula IV in benzene or methylene chloride at a temperature of from $-5°$ to $+10°$ C. and in the presence of boron trifluoride etherate and optionally a water-absorbing agent such as magnesium sulfate.

The dithioacetals V so obtained may then be purified by distillation or chromatography, or reacted directly with a diol of formula VI in inert solvents such as benzene or toluene, in the presence of acidic catalysts and optionally in the presence of water-absorbing agents to form the ketals of formula VII. A preferred embodiment of the process of the invention is the following: the dithioacetal V is heated to boiling in benzene or toluene in a water separator and in the presence of an acidic catalyst such as p-toluenesulfonic acid with an amount of a diol VI slightly above the quantity calculated, and subsequently worked up in usual manner.

The ketals of formula VII may be purified by distillation under highly reduced pressure or by chromatography, and subsequently reduced in known manner to the aldehydes of formula VIII. For this process step, all reducing agents known for the reduction of nitriles to aldehydes, preferably complex metal hydrides such as lithium-triethoxy-aluminum hydride, are suitable. Particularly preferred is di-isobutyl-aluminum hydride in inert solvents such as aliphatic or aromatic hydrocarbons or anhydrous ethers such as diethyl ether, tetrahydrofuran or 1,2-dimethoxy-ethane.

The reduction is carried out at a temperature of from $-40°$ to $+40°$ C., preferably from $-10°$ to $+10°$ C.

The reduction of VII may be carried out for example as follows: the equimolar amount or a slight excess of di-isobutyl-aluminum hydride is added dropwise to a solution of VII in toluene at a temperature of from $-5°$ to $+5°$ C. After two to three hours, the reduction is generally complete, and the aldimine may be hydrolyzed by adding glacial acetic acid and water to form the aldehyde VIII.

The aldehydes of formula VIII may be used directly for the next process step without special purification. Optionally, they may be purified by column chromatography. The reaction of the phosphonates of formula IX with compounds of formula VIII may be carried out under the conditions usual for the Horner reaction, for example in ethers at room temperature. Preferred ether are diethyl ether, tetrahydrofuran or dimethoxyethane. For a thorough completion of the reaction, the phosphonate is employed in excess.

Generally, the reaction is complete after 3 to 24 hours at a temperature of from 20° to 50° C. The reaction product of formula X is then isolated from the reaction mixture and purified according to known methods. Details on this reaction are described in J. Amer. Chem. Soc. 83, 1733 (1961).

The phosphonates of formula IX are either known (J. Org. Chem. 30, 680 (1965)), or they may be prepared in analogy to known processes (for example J. Amer. Chem. Soc. 88, 5654 (1966)).

Compounds of formula XI can be obtained by treating the compounds of formula X with a reducing agent. All those reducing agents may be employed which allow a selective reduction of a keto group to a hydroxyl group in the presence of an olefinic double bond. Preferred reducing agents are complex metal hydrides, especially boron hydrides such as potassium or sodium boron hydride, zinc boron hydride or lithium-perhydro-9b-bora-phenalkyl hydride (J. Amer. Chem. Soc. 92, 709 (1970)), or aluminum hydrides such as sodium-bis-(2-methoxyethoxy)-aluminum hydride or di-isobutyl-aluminum hydride. Generally, the reduction is carried out at a temperature of from −10° to 50° C. in solvents inert to the hydrides, such as ethers, for example diethyl ether, dimethoxy-ethane, dioxan, tetrahydrofuran or di-ethyleneglycol-dimethyl ether, or hydrocarbons such as benzene, or in an alcohol/water mixture such as ethanol/water.

The aldehydes XII may be prepared from the dithioacetals XI in a mixture of an organic solvent with water in the presence of salts of heavy metals such as $HgCL_2$ or an alkyl halide. As organic solvents, there may be used especially those which are miscible with water, for example THF or dioxan, preferably dipolar aprotic solvents such as acetonitrile or DMF. Th protecting group is advantageously split off in the presence of an acid-binding agent. The reaction temperatures are from 0° to 100° C., preferably from 10° to 60° C.

According to an especially preferred embodiment of the process, the dithioketals XI are stirred in a DMF/water mixture with excess methyl iodide and calcium carbonate for 2 to 5 hours at 30° to 50° C. The aldehydes of formula XII so obtained may be directly reacted in further steps or purified by chromatography after the inorganic salts and the solvent have been eliminated.

The aldehydes of formula XII are converted to compounds of formula XIV by reaction with a phosphonium-ylide of formula XIII (wherein th radical $R^6$ is preferably phenyl) in an appropriate solvent. The phosphonium-ylides and the phosphonium salts on which they are based are prepared according to analogous methods described in the lterature (for example Organic Reactions, Vol. 14 (1965), p. 270 sqq., ed. John Wiley and Sons, New York, London, Sidney).

The solution of the resonance stabilized ylide of formula XIII is added in a slight excess to the solution of the aldehyde XII, and the reaction mixture is heated for 2 to 12 hours to 40°–100° C. As solvents, there may be used for example ethers such as diethyl ether, tetrahydrofuran, diethyleneglycol-dimethyl ether, di-lower alkyl sulfoxides such as dimethyl sulfoxide, or amides of carboxylic acids such as dimethyl formamide, dimethyl acetamide or hexamethylphosphoric acid triamide (HMPT), or hydrocarbons, especially benzene, toluene or xylene.

A preferred embodiment of the process of the invention is the following: a solution of the methoxycarbonylmethylenetriphenylphosphorane in toluene is added dropwise and in a slight excess to the solution of the aldehyde XII in toluene, and the reaction mixture is heated for 4 to 6 hours at 40°–80° C. in an inert gas atmosphere, for example under an argon blanket, and the completion of the reaction is determined by means of thin layer chromatography. After usual work-up, the compounds of formula XIV so obtained are purified by chromatography; however, they may also be employed in the form of crude products.

The ketal protecting group may be split off under gentle conditions, for example in an alcohol/water mixture and at temperatures of from 0° to 30° C. Generally, the protecting group is split off at temperatures of from 20° to 50° C. and a reaction time of 3 to 24 hours. After evaporation of the solvent at low temperatures, the ketonic acids or their esters are advantageously purified by chromatography; however, they may be further reacted directly after the acidic catalyst is removed, for example by distribution of the crude product in water or saturated sodium chloride solution on the one hand and in a nonpolar solution such as benzene on the other.

Under these conditions, the $\alpha,\beta$-unsaturated esters of formula I are in general hard to saponify.

In order to obtain compounds of formula I wherein $R^3$ is H, an alkaline saponification with an alkali lye in an aqueous-alcoholic solution is advantageously carried out subsequently.

Starting from compounds of formula I, wherein $R^1$ is H, the corresponding esters may be prepared very simply according to known methods by reaction of the carboxylic acids with a diazoalkane in a solvent such as diethyl ether or THF. Aromatic solvents such as benzene, or halogenated hydrocarbons such as chloroform are also suitable for these reactions.

A further possibility for preparing these esters consists in the reaction of salts of the carboxylic acids with an alkyl halide. Suitable solvents for this operation mode are especiallly dipolar, aprotic solvents such as acetonitrile, dimethyl formamide or dimethyl sulfoxide; the reaction temperatures are in a range of from −10° to +100° C., preferably from 20° to 60° C.

According to these methods, in principle any carboxylic acids of formula I may be converted to the corresponding esters.

Compounds of formula I wherein $R^1$ is H may be converted to the corresponding metal or ammonium salts by adding the equimolar amount of a base, a carbonate or an amine. Suitable amines are physiologically tolerable primary, secondary or tertiary amines such as triethylamine, benzylamine, tris-(hydroxymethyl)-methylamine, piperidine or 4-ethylmorpholine. Suitable metal ions are those of the alkali metals and alkaline earth metals.

The ester so obtained or the salt of the formula I, wherein $R^3$ is H, may be subsequently reacted with suitable acylating agents.

Such suitable acylating agents are the free carboxylic acids or the reactive derivatives thereof. When the carboxylic acid is used, the reaction is preferably carried out in this acid as solvent, at temperatures of from 0° to 70° C. In some cases it is advantageous to buffer the reaction solution in order to prevent secondary reactions (see J. E. Pike, F. H. Lincoln, W. P. Schneider, J.Org.Chem. 34, 3553, (1969)).

Furthermore, the corresponding carboxylic acid anhydrides may be used for the acylation. In this case, the reaction is preferably carried out in aprotic solvents in the presence of a base at temperatures of from 0° to 80° C. In order to obtain the compounds of the invention the alcohols may furthermore be reacted with the corresponding ketenes, and this reaction is also carried out in aprotic solvents at room temperature.

In the compounds II, III, V, VII, VIII, X, XI, XII and XIV, the side chains in 2- and 3-position of the cyclopentane ring may be arranged in cis- or trans-position to each other. After the ketal protecting group in 1-position of the cyclopentane ring has been split off however, the trans-arrangement of the two side chains preferably occurs because of thermodynamic reasons. When therefore compounds of formula I are treated with bases, compounds with side-chains in trans-position to each other are preponderantly obtained. Generally, the trans-arrangement of the side chains is obtained already on preparation and purification of these compounds.

The reactions for incorporating the double bonds do not proceed in a completely stereospecific manner. However, it is to be supposed that the Horner reaction, because of the specific operation mode, produces substantially a translinkage and the corresponding cis-product to an only insignificant extent, which latter is then eliminated by chromatographic purification steps. In a similar manner, the corresponding trans-olefin is obtained in the Witting reaction for the incorporation of the carboxyl side chain. Also in this case, the cis-olefin occuring to a small extent as by-product may be separated by corresponding purification operations.

By reducing the ketone X to the alcohol XI, a further chiral center is introduced into the molecule, so that the compounds of the formulae XI, XII, XIV and I are mixtures of compounds being diastereomeric with respect to this center. In principle these diastereomers may be separated in any of the cited steps. However, it is advantageous to separate the diastereomers in the step of the alcohols of formula I ($R^3=H$). Chromatographic methods are especially suitable for this separation of the isomers called α-isomers (more polar compound) and β-isomers (less polar compound).

To the extent that the individual reaction products are not obtained already in sufficiently pure form so that they may be used directly for the next reaction step, their purification by means, for example, of column, thin layer or high pressure liquid chromatography is recommended.

The compounds of formula I in accordance with this invention are generally obtained in the form of the racemates, which, optionally, may be obtained in the form of the optically active antipodes according to the usual methods of racemate separation.

The compounds of the invention are distinguished on the one hand by spasmogenic properties, and on the other by broncho-dilating, blood pressure lowering, luteolytic, abortive properties as well as properties inhibiting the secretion of gastric juice. They may therefore be used as medicaments.

The compounds of formula I in accordance with this invention may be administered in the form of free acids, their physiologically tolerable inorganic or organic salts or esters.

Acids and their salts or esters may be used in the form of aqueous solutions or suspensions thereof or dissolved or suspended in pharmacologically tolerable organic solvents such as monohydric alcohols or polyols, for example ethanol, ethyleneglycol or glycerol, oils such as sunflower oil or cod-liver oil, ethers such as diethyleneglycol-dimethyl ether, or polyethers such as polyethyleneglycols, or alternatively in the presence of other pharmacologically tolerable polymer carriers such as polyvinyl-pyrrolidone.

Suitable preparation forms are the usual galenic infusion or injection solutions and tablets, as well as locally applicable preparations such as creams, emulsions, suppositories or, especially, aerosols.

A further application field for the novel compounds is the combination with other active substances, for example and especially the following: fertility regulating hormones and releasing hormones such as LH, FSH, oestradiol, LH-RH, diuretics such as furosemide, antidiabetics such as glycodiazine, tolbutamide, glibenclamide, pheninform, buformin, metformin; circulatory preparations in any sense, for example coronary dilators such as chromonar or prenylamine, blood pressure lowering products such as reserpin, α-methyl-dopa or clonidines or antiarrhythmics, lipid lowering products, geriatrics and other preparations having effect on the metabolism, psychophmacological agents uch as chlorodiazepoxide, diazepam or mepromate, or vitamins, or prostaglandins or prostaglandin-like compounds, furthermore, prostaglandin antagonists and prostaglandin biosynthesis inhibitors such as non-steroid antiphlogistics.

The suitable daily dose is 1microgrmae to 10 mg/kg body weight, the suitable dosage unit is 0.05 mg to 200 mg of the active substance of the formula I.

The compounds of the formulae II, III, V, VII, VIII, X, XI, XII and XIV, are novel interesting intermediate compounds of the manufacture of compounds of formula I.

The following Examples illustrate the invention.

EXAMPLE 1

1-(5-acetoxypentyl)-2-oxo-cyclopentane-carboxylic acid ethyl ester 170 g [1.23 mols] of potassium carbonate were added to 180 g [1.15 mols] of 2-oxo-cyclopentane-carboxylic acid ethyl ester in 300 ml of dimethyl formamide, 281.5 g [1.1 mols] of 5-acetoxypentyl iodide were added dropwise and the mixture was heated at 100° C. for 4 hours. The solvent was distilled off under reduced pressure, the residue digested in diethyl ether, the solvent decanted off the solid residue, the ether washed with water, dried over $Na_2SO_4$ and distilled off under reduced pressure.

300 g of crude 1-(5-acetoxypentyl)-2-oxo-cyclopentanecarboxylic acid ethyl ester were obtained which were used for the following reaction without further purification.

EXAMPLE 2

2-(5-acetoxypentyl)-cyclopentanone 300 g of 1-(5-acetoxypentyl)-2-oxo-cyclopentane-carboxylic acid ethyl ester were refluxed for 5 hours in 1.5 l of acetic acid, 600 ml of water and 300 g of sulfuric acid. Subsequently, the solution was concentrated under reduced pressure, 1liter of semi-saturated sodium chloride solution was added, and the solution was extracted with acetic acid ethyl ester. The organic phase was washed with 500 ml of saturated sodium chloride solution and dried over sodium sulfate. 50 ml of acetic anhydride were added, and the whole was refluxed for 4 hours. The solvent was distilled off under reduced pressure and the residue was subjected to fractional distillation under reduced pressure in a column having a height of 30 cm.

170 g of a light colored oil having a boiling point of 113°–117° C. at 0.7 mm Hg were obtained.

EXAMPLE 3

2-(5-acetoxypentyl)-cyclopent-2-enone 161 g [0.76 mol] of 2-(5-acetoxypentyl)-cyclopentanone were dissolved in 440 ml of carbon tetrachloride, and a solution of 76 ml [0.935 mol] of sulfuryl chloride in 75 ml of carbon tetrachloride was added dropwise, while stirring at 10°–15° C., and the whole was stirred for 4 hours at room temperature. The solvent was distilled off under reduced pressure, the residue dissolved in toluene, washed with water and bicarbonate solution and dried over magnesium sulfate. 150 ml [1.25 mols] of 2,4,6-trimethylpyridine were added to the filtered solution, which was then refluxed, while stirring, for 15 hours. After cooling, the solution was washed twice with 2 n HCl, once with water and once with sodium bicarbonate solution, dried over sodium sulfate, filtered, and the solvent was distilled off under reduced pressure. The residue was distilled under a reduced pressure of 0.5 mm in a column having a length of 10 cm, and 106 g having a boiling point of 120°–125° C. at 0.5 mm Hg were obtained.

EXAMPLE 4

2-(5-acetoxypentyl)-3-oxo-cyclopentane-carbonitrile 98 g [1.5 mols] of potassium cyanide were suspended in 600 ml of methanol, and 105 g [0.5 mol] of 2-(5-acetoxypentyl)- cyclopent-2-ene-1-one, dissolved in 45 ml of acetic acid, were added dropwise within 2.5 hours. After 20 hours, agitation at room temperature, the suspension was dropped into ice-water with agitation, extracted thrice with diethyl ether, the ether phases were united, washed with water, dried over sodium sulfate and concentrated. The oily residue was stirred for 5 hours at room temperature in 200 ml of pyridine and 30 ml of acetic anhydride, the solvent was then distilled off under reduced pressure and the residue was distilled in a bulb tube. 102 g having a boiling point of 180° C. at 0.4 mm Hg were obtained; IR spectrum: 2220 cm$^{-1}$.

EXAMPLE 5.

2-(5-hydroxypentyl)-3-oxo-cyclopentane-carbonitrile 102 g of 2-(5-acetoxypentyl)-3-oxo-cyclopentane-carbonitrile were stirred for 16 hours at room temperature in 1 l of methanol with 5 ml of concentrated sulfuric acid, 10 g of NaHCO$_3$ were added, the solvent was concentrated under reduced pressure, the oily residue was absorbed in acetic acid ester, washed with water and concentrated.

84.7 g of crude product were obtained which were directly used for the following reaction without any purification. For characterization, an analysis sample was distilled under reduced pressure.

IR: 3400 cm$^{-1}$ (OH); 2240 cm$^{-1}$ (CN)

EXAMPLE 6

2-(4-formylbutyl)-3-oxo-cyclopentane-carbonitrile 19.5 g [0.1 mol] of 2-(5-hydroxy-pentyl)-3-oxo-cyclopentane-carbonitrile in 30 ml of toluene were added dropwise at −10° to −15° C. to a suspension of [0.5 mol]=66.8 g of N-chlorosuccinimide and [0.6 mol]=43.8 ml of dimethyl sulfide in 200 ml of absolute toluene, stirred for 3 hours at −10° to −14° C., subsequently about 75 ml [0.6 mol] of triethylamine were added, agitation was continued for one hour at −10° C., and the reaction mixture was added to the icecold saturated sodium chloride solution. The organic phase was separated, washed to neutral with 1 n HCl, dried and concentrated. 17 g of aldehyde were obtained.

An analysis sample was subjected to chromatography on silica gel.

NMR δ 9.7, broad signal, 1 H.

EXAMPLE 7

2-[4-(1,3-dithia-2-cyclopentyl)-butyl]-3-oxo-cyclopentane-carbonitrile 17 g [0.063 mol] of 2-(4-formylbutyl)-3-oxo-cyclopentane-carbonitrile were dissolved in 200 ml of toluene and stirred for 30 minutes at room temperature with [0.08 mol]=6.7 ml of 1,2-ethanedithiol and 2 ml of boron trifluoride etherate, washed with water and sodium bicarbonate solution, dried over sodium sulfate and concentrated. 15.6 g of a light color oil were obtained.

An analysis sample was subjected to chromatography on silica gel.

NMR δ 3.2 ppm, singlet, 4 H 4.3–4.6 ppm, triplet, 1 H.

EXAMPLE 8

7-{6-[4-(1,3-dithia-2-cyclopentyl)butyl]-1,4-dioxaspiro[4,4] nonane} carbonitrile 6.8 g [0.024 mol] of 2-[4-(1,3-dithia-2-cyclopentyl)-butyl]-3-oxo-cyclopentane-carbonitrile were refluxed for 4 hours in a water separator in 200 ml of toluene with 10 ml of 1,2-ethanediol and 3 ml of boron trifluoride etherate, further 10 ml of 1,2-ethanediol and 3 ml of boron trifluoride etherate were added and the whole was again refluxed for 3 hours. After cooling, the solution was added to icewater, the organic phase was diluted with diethyl ether and washed with a 5% sodium bicarbonate solution. After drying over magnesium sulfate, the solvent was distilled off under reduced pressure, and 6.4 g of a light color oil were obtained. The analysis sample obtained by chromatography had the following characteristic bands in the NMR spectrum:

δ4.4–4.7 ppm, triplet, 1 H; 3.9 ppm, singlet, 4 H; 3.2 ppm, singlet, 4 H.

EXAMPLE 9

7-{6-[4-(1,3-dithia-2-cyclopentyl)butyl]-1,4-dioxaspiro[4,4]-nonane}carbaldehyde 13.3 g [0.042 mol] of 7-{6-[4-(1,3-dithia-2-cyclopentyl)-butyl]-1,4-dioxaspiro[4,4]nonane} carbonitrile were dissolved in 200 ml of toluene, cooled to 5° C., and 9 g [0.064 mol]=53 ml of 20% diisobutyl-aluminum hydride solution in toluene were added dropwise and slowly in such a manner that the temperature did not exceed 7° C. After a reaction time of 2 hours, 15 ml of glacial acetic acid in 30 ml of toluene were added dropwise, subsequently also 50 ml of water, and the whole was stirred for another 30 minutes. The reaction mixture was then filtered by means of a clarifying layer filter, the organic phase was diluted with ether and separated from the water. After drying over sodium sulfate, the solvent was distilled off under reduced pressure, and 11 g of oily aldehyde were obtained.

The analysis sample was subjected to chromatography on silica gel and showed the following characteristic signals in the NMR spectrum:

δ 9.5–9.7 ppm, doublet, 1 H, 4.3–4.6 ppm, triplet, 1 H; 3.9 ppm, singlet, 4 H; 3.2 ppm, singlet, 2 H.

EXAMPLE 10a

1-{6-[4-(1,3-dithia-2-cyclopentyl)butyl]1,4-dioxaspiro[4,4]-non-7-yl}-4,4-dimethyl-6-oxa-1-trans-octene-3-one

[30 millimols] ≙ 870 mg of 80% sodium hydride suspension were suspended in 90 ml of glycol-dimethyl ether, and [25 millimols] ≙ 6.3 g of dimethyl-2-oxo-3,3-dimethyl-5-oxa-heptyl phosphonate were added, and the whole was stirred for 2 hours at room temperature. To this reaction mixture so obtained a solution of [20 millimols] ≙ 6.32 g of 7-{6-[4-(1,3-dithia-2-cyclopentyl)butyl]-1,4-dioxaspiro[4,4]nonane}-carbaldehyde in 60 ml of glycoldimethyl ether was added dropwise, and the whole was stirred for 3 hours at room temperature. Acetic acid was added until a sample reacted neutral in water. Some animal charcoal was added, the whole was suction-filtered, and evaporated under reduced pressure.

The residue was subjected to chromatography on silica gel and obtained by elution with toluene/acetic acid ester in a 10:1 ratio. 6.8 g of a light yellow oil were obtained. NMR: δ 6.6–7.1 ppm, double doublet 1 H; 6.2–6.6 ppm, doublet 1 H; 4.6 ppm, triplet 1 H; 3.9 ppm, singlet 4 H; 3.0–3.7 ppm, quartet and 2 singlets 8 H.

EXAMPLE 10b

In analogous manner, 1-{-6-[4-(1,3-dithia-2-cyclopentyl)-butyl]-1,4-dioxaspiro[4,4] non-7-yl}-4,4-dimethyl-5-oxa-1-trans-octen-3-one was prepared by reaction of dimethyl-2-oxo-3,3-dimethyl-4-oxa-heptyl-phosphonate.

NMR: δ 6.5–7.4 ppm, multiplet 2 H; 3.3 ppm, triplet 2 H; 1.3 ppm, singlet 6 H.

EXAMPLE 10c

In analogous manner, 1-{6-[4-(1,3-dithia-2-cyclopentyl)-butyl]-1,4-dioxaspiro[4,4]non-7-yl}-4,4-dimethyl-7-oxa-1-trans-octen-3one was prepared by reaction of dimethyl-2-oxo-3,3-dimethyl-6-oxa-heptyl-phosphonate.

NMR: δ 6.0–7.2 ppm, multiplet 2 H; 3.2 ppm, singlet 3 H; 3.1–3.5 ppm, multiplet 2 H; 1.2 ppm, singlet 6 H.

EXAMPLE 10d

In analogous manner, 1-{6-[4-(1,3-dithia-2-cyclopentyl)-butyl]-1,4-dioxaspiro[4,4]-non-7-yl}-4-methyl-7-oxa-1-trans-octen-3-one was prepared by reaction of dimethyl-2-oxo-3-methyl-6-oxa-heptylphosphonate.

NMR: δ 6.6–7.1 ppm, double doublet 1 H; 6.0–6.4 ppm, doublet 1 H; 3.0–3.6 ppm, triplet with singlet 5 H; 1.1 ppm, doublet 3 H.

EXAMPLE 10e

In analogous manner, 1-{6-[4-(1,3-dithia-2-cyclopentyl)-butyl]-1,4-dioxaspiro[4,4]-non-7-yl}-4,4-dimethyl-6-oxa-1-trans-nonen-3-one was prepared by reaction of dimethyl-2-oxo-3,3-dimethyl-5-oxa-octylphosphonate.

NMR: δ 6.2–7.3 ppm, doublet and double doublet 2 H; 3.4 ppm, singlet 2 H; 3.3 ppm, triplet 2 H; 1.2 ppm, singlet 6 H; 0.8 ppm, triplet 3 H.

EXAMPLE 10f

In analogous manner, 1-{6-[4-(1,3-dithia-2-cyclopentyl)-butyl]-1,4-dioxaspiro[4,4]-non-7-yl}-4,4-dimethyl-6oxa-1-trans-decen-3-one was prepared by reaction of dimethyl-2-oxo-3,3-dimethyl-5-oxa-nonylphosphonate.

NMR: δ 6.1–7.3 ppm, doublet and double doublet 2 H; 3.2–3.6 ppm, triplet and singlet 4 H; 1.2 ppm, singlet 6 H; 0.9 ppm, broad triplet 3 H.

EXAMPLE 10g

In analogous manner, 1-{6-[4-(1,3-dithia-2-cyclpentyl)-butyl]-1,4-dioxaspiro[4.4]-non-7-yl}-4,4-dimethyl-6-oxa-1-trans-hepten-3-one was prepared by reaction of dimethyl-2-oxo-3,3-dimethyl-5oxa-hexylphosphonate.

NMR: δ 6.1–7.3 ppm, doublet and double doublet 2 H; 3.4 ppm, singlet 2 H; 3.3 ppm, singlet 3 H; 1.2 ppm, singlet 6 H.

EXAMPLE 10h

In analogous manner, 1-{6-[-(1,3-dithia-2-cyclopentyl)-butyl]-1,4-dioxaspiro[4.4]-non-7-yl}-4,4,8-trimethyl-6-oxa-1-trans-nonen-3-one was prepared by reaction of dimethyl-2-oxo-3,3,7-trimethyl-5-oxa-octylphosphonate.

NMR: δ 6.1–7.3 ppm, doublet and double doublet 2 H; 3.4 ppm, singlet 2 H; 3.0–3.2 ppm, doublet 2 H; 1.2 ppm, singlet 6 H; 0.7–0.9 ppm, doublet 6 H.

EXAMPLE 10i

In analogous manner, 1-{6-[4-(1,3-dithia-2-cyclpentyl)-butyl]-1,4-dioxaspiro[4.4]-non-7-yl}-6-oxa-1-trans-octen-3-one was prepared by reaction of dimethyl-2-oxo-5-oxa-heptylphosphonate.

NMR: δ 6.0–7.3 ppm, doublet and double doublet 2 H; 3.2–4.0 ppm, multiplet 4 H; 1.0–1.4 ppm, triplet 3 H.

EXAMPLE 11a

1-{6-[4-(1,3-dithia-2-cyclopentyl)butyl]-1,4-dioxaspiro[4.4]-non-7-yl}-4,4-dimethyl-6-oxa-1-trans-octene-3-ole 7.9 g [18 millimols] of 1-{6-[4-(1,3-dithia-2-cyclopentyl)-butyl]-1,4-dioxaspiro[4.4]-non-7-yl}-4,4-dimethyl-6-oxa-1-trans-octene-3-one were dissolved in 120 ml of methanol. This solution was added dropwise to a solution of 3.4 g of sodium-boron hydride in 55 ml of 90% aqueous methanol prepared at 0° C., and the reaction mixture was then stirred for 2 hours at room temperature, neutralized at 0° C. with glacial acetic acid, and the methanol was distilled off at room temperature. The residue was dissolved in diethyl ether and washed once with water and once with half saturated sodium bicarbonate solution. The ether solution was dried over magnesium sulfate and evaporation was carried out. 7.2 g of a colorless oil were obtained.

NMR: δ 5.4–5.6 ppm, multiplet 2 H; 4.4 ppm, triplet 1 H; 3.8–3.0 ppm, singlet and multiplet 5 H; 3.0–3.8 ppm, quartet and 2 singlets 8 H; 1.2 ppm, triplet 3 H; 0.9 ppm, singlet 6 H.

EXAMPLE 11b

In analogous manner, 1-{6-[4-(1,3-dithia-2-cyclopentyl)-butyl]-1,4-dioxaspiro[4.4]-non-7-yl}-4,4-dimethyl-5-oxa-1trans-octen-3-one was converted to 1-{6-[4-(1,3-dithia-2-cyclopentyl)-butyl]-1,4-dioxaspiro[4.4]-non-7-yl}-4,4-dimethyl-5-oxa-1-trans-octen-3-ole.

IR: 3500 cm$^{-1}$, no carbonyl band

NMR: δ 5.5–5.9 ppm, multiplet 2 H.

EXAMPLE 11c

In analogous manner, 1-{6-[4-(1,3-dithia-2-cyclopentyl)-butyl]-1,4-dioxaspiro[4.4]-non-7-yl}-4,4-dimethyl-7oxa-1-trans-octen-3-one was converted to 1-{6-[4-(1,3- dithia-2-cyclopentyl)-butyl]-1,4-dioxaspiro-[4.4]non-7-yl}-4,4-dimethyl-7-oxa-1-trans-octen-3-ole.

IR: 3500 cm$^{-1}$, no keto band
NMR: δ 5.5–5.9 ppm.

EXAMPLE 11d

In analogous manner, 1-{6-[4-(1,3-dithia-2-cyclopentyl)-butyl]-1,4-dioxaspiro[4.4]-non-7-yl}-4-methyl-7oxa-1-trans-octen-3-one was converted to 1-{6-[4-(1,3-dithia-2-cyclopentyl)-butyl]-1,4-dioxaspiro-[4.4]-non-7-yl}-4-methyl-7oxa-1-trans-octen-3-ole.

IR: 3500 cm$^{-1}$, no keto band.
NMR: 5.5–5.9 ppm, 2 H.

EXAMPLE 11e

In analogous manner, 1-{6-[4-(1,3-dithia-2-cyclopentyl)-butyl]-1,4-dioxaspiro[4.4]-non-7-yl}-4,4-dimethyl-6oxa-1-trans-nonen-3-one was converted to 1-{6-[4-(1,3-dithia-2-cyclopentyl)-butyl]-1,4-dioxaspiro[4.4]-non-7-yl}-4,4-dimethyl-6-oxa-1-trans-nonen-3-ole.

IR: 3500 cm$^{-1}$, no carbonyl band.
NMR: δ 5.5–5.9 ppm 2 H.

EXAMPLE 11f

In analogous manner, 1-{6-[4-(1,3-dithia-2-cyclopentyl)-butyl]-1,4-dioxaspiro[4.4]-non-7-yl}-4,4-dimethyl-6-oxa-1-trans-decen-3-one was converted to 1-{6-[4-(1,3-dithia-2-cyclopentyl)-butyl]-1,4-dioxaspiro[4.4]-non-7-yl}-4,4-dimethyl-6-oxa-1-trans-decen-3-ole.

IR: 3500 cm$^{-1}$, no carbonyl band
NMR: δ 5.5–5.5 ppm, 2 H.

EXAMPLE 11g

In analogous manner, 1-{6-[4-(1,3-dithia-2-cyclopentyl)-butyl]-1,4-dioxaspiro[4.4]-non-7-yl}-4,4-dimethyl-6-oxa-1-trans-hepten-3-one was converted to 1-{6-[4-(1,3-dithia-2-cyclopentyl)-butyl]-1,4-dioxaspiro[4.4]-non-7-yl}-4,4-dimethyl-6oxa-1-trans-hepten-3-ole.

IR: 3500 cm$^{-1}$, no carbonyl band.
NMR: δ 5.4–5.9 ppm, 2 H.

EXAMPLE 11h

In analogous manner, 1-{6-[4-(1,3-dithia-2-cyclopentyl)-butyl]-1,4-dioxaspiro[4.4]-non-7-yl}-4,4,8-trimethyl-6oxa-1-trans-nonen-3-one was converted to 1-{6-[4-(1,3-dithia-2-cyclopentyl)-butyl]-1,4-dioxaspiro[4.4]-non-7-yl}-4,4,8-trimethyl-6oxa-1-trans-nonen-3-ole.

IR: 3500 cm$^{-1}$, no carbonyl band.
NMR: δ 5.3–5.9 ppm.

EXAMPLE 11i

In analogous manner, 1-{6-[4-(1,3-dithia-2-cyclopentyl)-butyl]-1,4-dioxaspiro[4.4]-non-7-yl}-6-oxa-1-trans-octen-3-one was converted to 1-{6-[4-(1,3-dithia-2-cyclopentyl)-butyl]-1,4-dioxaspiro[4.4]-non-7-yl}-6-oxa-1-trans-octen-3-ole.

IR 3500 cm$^{-1}$, no C=O band.
NMR: δ 5.4–6.0 ppm.

EXAMPLE 12a

5-[7-(3hydroxy-4,4-dimethyl-6-oxa-1-trans-octenyl)-1,4-dioxaspiro[4.4]non-7-yl]pentane aldehyde 4.1 g 1-{6-[4-(1,3-dithia-2-cyclopentyl)butyl]-1,4-dioxaspiro[4.4]non-7-yl}-4,4-dimethyl-6-oxa-1-trans-3-ole were dissolved in 4.1 ml of dimethyl sulfoxide. This solution was combined with 7.5 g of anhydrous calcium carbonate, 9.2 g of methyl iodide and 2 ml of water, and the batch was stirred for 3 hours at 60° C. Subsequently, it was allowed to cool, the reaction mixture was filtered via a clarifying layer filter and the filter residue was thoroughly washed with diethyl ether. The ether phase was washed with water and sodium thiosulfate solution, dried and evaporated to dryness at room temperature. 3.54 g of a light yellow oil were obtained.

DC (toluene/acetic acid ester 4:1).
Rf 0.23 stainable with 2,4-dinitrophenylhydrazine.
NMR: δ 9.8 ppm, triplet 1H; 5.4–5.8 ppm, multiplet 2H; 3.8–4.0 ppm, multiplet and singlet 5H; 3.7–3.2 ppm, quartet and singlet 4H; 1.2 ppm, triplet; 0.9 ppm, singlet 6H.

In completely analogous manner, the thioketals described in Examples 11b to 11i were converted to the corresponding aldehydes:

EXAMPLE 12b

5-[7-(3-hydroxy-4,4-dimethyl-5-oxa-1-trans-octenyl)-1,4-dioxaspiro[4.4]non-6-yl]-pentane-aldehyde.

TLC (toluene 4/acetic ester 1).
Rf ~ 0.24, stainable with 2,4-dinitrophenylhydrazine.

EXAMPLE 12c

5-[7-(3-hydroxy-4,4-dimethyl-7-oxa-1-trans-octenyl)-1,4-dioxaspiro-[4.4]non-6-yl]pentane-aldehyde TLC (toluene 4/acetic ester 1).
Rf ~ 0.26, stainable with 2,4-dinitrophenylhydrazine.

EXAMPLE 12d

5-[7-(3-hydroxy-4-methyl-7-oxa-1-trans-octenyl)-1,4-dioxaspiro-[4.4]-non-6-yl]-pentane-aldehyde TLC (toluene 4/acetic ester 1).
Rf ~ 0.25, stainable with 2,4-dinitrophenylhydrazine.

EXAMPLE 12e

5-[7-(3-hydroxy-4,4-dimethyl-6-oxa-1-trans-nonenyl)-1,4-dioxaspiro[4.4]-non-6-yl]-pentane-aldehyde TLC (toluene 4/ acetic ester1).
Rf ~ 0.24 stainable with 2,4-dinitrophenylhydrazine.

EXAMPLE 12f

5-[7-(3-hydroxy-4,4-dimethyl-6-oxa-1-trans-decenyl)-1,4-dioxaspiro[4.4]-non-6-yl]-pentane-aldehyde TLC (toluene 4/acetic ester 1).
Rf ~ 0.28 stainable with 2,4-dinitrophenylhydrazine.

EXAMPLE 12g

5-[7-(3-hydroxy-4,4-dimethyl-6-oxa-1-trans-heptenyl)-1,4-dioxaspiro[4.4]-non-6-yl]-pentane-aldehyde TLC (toluene 4/acetic ester 1).
Rf ~ 0.24, stainable with 2,4-dinitrophenylhydrazine.

EXAMPLE 12h

5-[7-(3-hydroxy-4,4,8-trimethyl-6-oxa-1-trans-nonenyl)-1,4-dioxaspiro[4.4]-non-6-yl]-pentane-aldehyde TLC (toluene 4/acetic ester 1).
Rf ~ 0.28, stainable with 2,4-dinitrophenylhydrazine.

EXAMPLE 12i

5-[7-(3-hydroxy-6-oxa-1-trans-octenyl)-1,4-dioxaspiro[4.4]-non-6-yl]-pentane-aldehyde DLC (toluene 4/acetic ester 1).
Rf ~ 0.24, stainable with 2,4-dinitrophenylhydrazine.

EXAMPLE 13a 9,9-Ethylenedioxy-15-hydroxy-16,16-dimethyl-18-oxa-prosta-2-trans,13-trans-dienic acid methyl ester 590 mg 5-[7-(3hydroxy-4,4-dimethyl-6-oxa-1-trans-octenyl)-1,4-dioxaspiro[4.4]-non-6-yl]-pentane-aldehyde were dissolved in 50 ml of absolute toluene, 645 mg of methoxycarbonyl-methylene-triphenyl-phosphorane were added, and the batch was refluxed for 3½ hours. Subsequently, the reaction solution was evaporated to dryness, the residue was absorbed in ether and filtered. The filtrate was evaporated and filtered via a column with silica gel by means of toluene/acetic acid ester 4/1. 671 mg of the intended final product were obtained.

NMR: $\delta$ 6.6–7.3 multiplet 1H; 5.3–5.8 multiplet with doublet 3H; 3.0–4.0 multiplet with 3 singlets 12H; quartet 1.1 triplet 3H; 0.8 singlet 6H.

EXAMPLE 13b 9,9-Ethylenedioxy-15-hydroxy-16,16-dimethyl-17-oxa-prosta-2-trans,13-trans-dienic acid methyl ester was obtained from the compound described in Example 12b.

NMR: The olefinic protons of the new double bond appear at $\delta$ 6.6–7.4 (double triplet) and $\delta$ 5.5–6.1 (doublet, one line together with the protons of the 13,14-double bond).

TLC: (toluene 4/acetic ester 1).
Rf~ 0.29.

EXAMPLE 13c 9,9-Ethylenedioxy-15-hydroxy-16,16-dimethyl-19-oxa-prosta-2-trans,13-trans-dienic acid methyl ester from the compound of Example 12c.

NMR: $\delta$ 6.6–7.4 1H, 5.4–6.2 3H.

EXAMPLE 13d 9,9-Ethylenedioxy-15-hydroxy-16-methyl-19-oxa-prosta-2-trans,13-trans-dienic acid methyl ester from the compound of Example 12d.

NMR: $\delta$ 6.5–7.4 1H, 5.4–6.2 3H.

EXAMPLE 13e 9,9Ethylenedioxy-15-hydroxy-16,16-dimethyl-18-oxa-20-homo-prosta-2-trans,13-trans-dienic acid methyl ester from the compound of Example 12e.

NMR: $\delta$ 6.6–7.4 1H; 5.4–6.2 3H.

EXAMPLE 13f 9,9-Ethylenedioxy-15-hydroxy-16,16-dimethyl-18-oxa-20-bis-homo-prosta-2-trans,13-trans-dienic acid methyl ester from the compound of Example 12f.

NMR: $\delta$ 6.6–7.4 1H; 5.4–6.2 3H.

EXAMPLE 13g 9,9-Ethylenedioxy-15-hydroxy-16,16-dimethyl-18-oxa-20-nor-prosta-2-trans,13-trans-dienic acid methyl ester from the compound of Example 12g.

NMR: $\delta$ 6.6–7.4 1H; 5.4–6.2 3H.

EXAMPLE 13h 9,9-Ethylenedioxy-15-hydroxy-16,16,20-trimethyl-18-oxa-20-homo-prosta-2-trans,13-trans-dienic acid methyl ester from the compound of Example 12h.

NMR: $\delta$ 6.5–7.4 1 H; 5.4–6.2 3 H.

EXAMPLE 13i 9,9-Ethylenedioxy-15-hydroxy-18-oxa-prosta-2-trans,13-trans-dienic acid methyl ester from the compound of Example 12i.

NMR: $\delta$ 6.5–7.4 1 H; 5.4–6.2 3 H.

EXAMPLE 14a

9-Keto-15-hydroxy-16,16-dimethyl-18-oxa-prosta-2-trans,13-trans-dienic acid methyl ester 325 mg 9,9-ethylenedioxy-15-hydroxy-16,16-dimethyl-18-oxa-prosta-2-trans,13-trans-dienic acid methyl ester were dissolved in 20 ml of methanol, and 2 ml of 10% aqueous oxalic acid were added. This mixture was stirred for 4 hours at 40° C. Subsequently, the reaction solution is evaporated to dryness at room temperature, and the residue is dissolved in diethyl ether. The ether solution is washed with half concentrated NaHCO$_3$ solution, dried, and evaporated to dryness. In order to separate the C-15 isomers, the residue is separated by chromatography on silica gel with toluene/acetic acid ester (4:1) as diluent. 158 mg of the less polar $\beta$-isomer and 127 mg of the $\alpha$-isomer and 32 mg of an $\alpha$, $\beta$-isomer mixture are obtained.

NMR: $\delta$ 6.6–7.3 multiplet 1H; 5.4–6.0 multiplet 3 H; 3.8–4.0 multiplet 1 H; 3.0–3.8 2 singlets, 1 quartet 7 H; 1.2 triplet 3 H; 0.9 singulet 6 H.

The NMR dates of the C-15 isomers are identical.

According to the method described in Example 14a, the following compounds were prepared:

EXAMPLE 14b 9-keto-15-hydroxy-16,16-dimethyl-17-oxa-prosta-2-trans,13-trans-dienic acid methyl ester NMR: $\delta$ 6.6–7.3 multiplet 1 H; 5.3–6.0 multiplet 3 H; 3.7–4.1 multiplet 1 H; 3.8 singlet 3 H; 3.0–3.7 large triplet 2H; 1.1 singlet 6 H.

EXAMPLE 14c 9-keto-15-hydroxy-16,16-dimethyl-19-oxa-prosta-2-trans,13-trans-dienic acid methyl ester NMR: $\delta$ 6.6–7.4 multiplet 1 H, 5.2–6.0 multiplet 3 H; 3.7–4.1 multiplet 1 H; 3.7 singlet 3 H; 3.0–3.7 triplet and singlet 5 H; 0.9 singlet 6 H.

EXAMPLE 14d 9-keto-15-hydroxy-16-methyl-19-oxa-prosta-2-trans,13-trans-dienic acid methyl ester NMR: $\delta$ 6.6–7.4 multiplet 1 H; 5.2–6.0 multiplet 3 H; 3.7–4,1 multiplet 1 H; 3.7 singlet 3 H; 3.0–3.7 triplet and singlet 5 H; 0.8–1.0 large doublet 3H.

EXAMPLE 14e 9-keto-15--hydroxy-16,16-dimethyl-18-oxa-20-homo-prosta-2-trans,13-trans-dienic acid methyl ester NMR: $\delta$ 6.6–7.4 multiplet 1 H; 5.2–6.0 multiplet 3 H; 3.7–4.1 multiplet 1 H; 3.7 singlet 3 H; 3.0–3.7 singlet and triplet 4 H; 09 singlet 6 H.

EXAMPLE 14f 9-keto-15-hydroxy-16,16-dimethyl-18-oxa-20-bis-homo-prosta-2-trans,13-trans-dienic acid methyl ester NMR: δ6.6–7.4 multiplet 1 H; 5.2–6.0 multiplet 3 H; 3.7–4.1 multiplet 1 H; 3.7 singlet 3 H; 3.0–3.7 singlet and triplet 4 H; 0.9 singlet 6 H.

EXAMPLE 14g 9-keto-15-hydroxy-16,16-dimethyl-18-oxa-20-nor-prosta-2-trans,13-trans-dienic acid methyl ester NMR: δ 6.6–7.4 multiplet 1 H; 5.2–6.0 multiplet 3 H; 3.7–4.1 multiplet 1 H; 3.7 singlet 3 H; 3.3 singlet 3 H; 3.2 singlet 2 H; 0.9–1.0 singlet 6 H.

EXAMPLE 14h 9-keto-15-hydroxy-16,16,20-trimethyl-18-oxa-20-homo-prosta-2-trans,13-trans-dienic acid methyl ester NMR: δ 6.6–7.4 multiplet 1 H; 5.2–6.0 multiplet 3 H; 3.7–4.1 multiplet 1 H; 3.7 singlet 3 H; 3.3 singlet 2 H; 3.1–3.3 doublet 2 H; 0.7–1.1 multiplet 12 H.

EXAMPLE 14i 9-keto-15-hydroxy-18-oxa-prosta-2-trans,13-trans-dienic acid methyl ester NMR: δ6.4–7.4 multiplet 1 H; 5.2–6.0 multiplet 3 H; 3.8–4.3 multiplet 1 H; 3.7 singlet 3 H; 3.3–3.8 multiplet 4 H; (triplet and quartet) 1.3 triplet 3 H.

EXAMPLE 15a 9-keto-15-hydroxy-16,16-dimethyl-18-oxa-prosta-2-trans,13-trans-dienic acid 220 mg 9-keto-15-hydroxy-16,16-dimethyl-18-prosta-2-trans,13-trans-dienic acid methyl ester were dissolved in 5 ml of methanol and 1 ml of 1 N NaOH solution was added. This reaction mixture was refluxed for ½ hours. After cooling, the main amount of methanol was evaporated under reduced pressure at room temperature and subsequently, 5 ml of water were added. The aqueous solution so obtained was twice extracted with diethyl ether. The solution so freed from non-acidic substances was acidified with 10% aqueous citric acid, and several times extracted with ether. The united ether phases were dried and evaporated. The residue was subjected to chromatograhy on silica gel with acetic acid ester/cyclohexane/glacial acetic acid 40:60:1. 133 g of pure product were obtained.

NMR: δ6.6–7.3 multiplet 1 H; 5.0–6.0 multiplet 5 H; 3.8–4.0 multiplet 1 H; 3.0–3.8 2 singlet 7 H; 1 quartet 1.2 triplet 3 H; 0.9 singlet 6 H;

EXAMPLE 15b 9-keto-15-hydroxy-16,16-dimethyl-17-oxa-prosta-2-trans,13-trans-dienic acid.

NMR: δ7.3–7.8 multiplet 2 H; 6.7–7.4 multiplet 1 H; 5.4–6.0 multiplet 3 H; 4.1–4.4 multiplet 1 H; 3.2–3.7 large triplet 2 H.

EXAMPLE 15c 9-keto-15-hydroxy-16,16-dimethyl-19-oxa-prosta-2-trans,13-trans-dienic acid NMR: δ7.3–7.8 multiplet 2 H; 6.7–7.4 multiplet 1 H; 5.2–6.0 multiplet 3 H; 3.8–4.1 multiplet 1 H; 3.0–3.5 singlet and large triplet 5 H.

EXAMPLE 15d 9-keto-15-hydroxy-16-methyl-19-oxa-prosta-2-trans,13-trans-dienic acid NMR: δ7.3–7.8 multiplet 2 H; 6.7–7.4 multiplet 1 H; 5.2–6.0 multiplet 3 H; 3.0–3.7 singlet and triplet 5 H; 3.9–4.2 multiplet 1 H; 0.8–1.0 large doublet 3 H.

EXAMPLE 15e 9-keto-15-hydroxy-16,16-dimethyl-18-oxa-20-homo-prosta-2-trans,13-trans-dienic acid NMR: δ7.3–7.8 multiplet 2 H; 6.7–7.4 multiplet 1 H; 5.2–6.0 multiplet 3 H; 3.9–4.1 multiplet 1 H; 3.2–3.8 singlet and triplet 4 H; 0.9 singlet 6 H.

EXAMPLE 15f 9-keto-15-hydroxy-16,16-dimethyl-18-oxa-20-bis-homo-prosta-2-trans,13-trans-dienic acid NMR: δ7.3–7.8 multiplet 2 H; 6.7–7.4 multiplet 1 H; 5.2–6.0 multiplet 3 H; 3.8–4.1 multiplet 1 H; 3.1–3.8 singlet and triplet 4 H; 0.9 singlet 6 H.

EXAMPLE 15g 9-keto-15-hydroxy-16,16-dimethyl-18-oxa-20-nor-prosta-2-trans,13-trans-dienic acid NMR: δ7.3–7.8 multiplet 2 H; 6.7–7.4 multiplet 1 H; 5.2–6.0 multiplet 3 H; 3.9–4.1 multiplet 1 H; 3.4 singlet 3 H; 3.3 singlet 2 H; 0.9 singlet 6 H.

EXAMPLE 15h 9-keto-15-hydroxy-16,16,20-trimethyl-18-oxa-20-homo-prosta-2-trans,13-trans-dienic acid NMR: δ7.4–7.8 multiplet 2 H; 6.7–7.4 multiplet 1 H; 5.2–6.0 multiplet 3 H; 3.7–4.1 multiplet 1 H; 3.0–3.4 singlet with doublet 4 H; 0.7–1.1 multiplet 12 H.

EXAMPLE 15i 9-keto-15-hydroxy-18-oxa-prosta-2-trans,13-trans-dienic acid

NMR: δ7.2–7.9 multiplet 2 H; 6.7–7.4 multiplet 1 H; 5.2–6.0 multiplet 3 H; 4.2–4.6 multiplet 1 H; 3.3–3.9 2 quartets 4 H.

EXAMPLE 16a

9-Keto-15α-acetoxy-16,16-dimethyl-18-oxa-prosta-2,13-dienic acid methyl ester 100 mg 9-keto-15α-hydroxy-16,16-dimethyl-18-oxa-prosta-2,13-dienic acid methyl ester were dissolved in 2 ml of absolute dimethoxy-ethane, and added dropwise to a mixture of 5 ml of dimethoxy-ethane, 2ml of pyridine and 1 ml of acetyl chloride prepared at 0° C. Stirring was continued for 5 hours at room temperature. Subsequently, the reaction mixture was substantially evaporated under reduced pressure at room temperature, the residue dissolved in ether and the ether solution washed in a sequence first with 5 ml of 10% aqueous citric acid and then with 5 ml of half saturated sodium bicabonate solution. The product is dried over magnesium sulfate and evaporated.

Yield: 96 mg.

TLC: (toluene/acetic ester 1/1): Rf~0.406.

NMR: δ7.2–6.6 ppm 1 H multiplet; 6.0–5.0 ppm 4 H multiplet; 3.7 ppm 3 H singlet; 3.3 ppm 2 H quartet; 3.1 ppm 2 H singlet; 2.5–0.7 ppm remaining H, multiplet with singlets at 2.0 ppm, 0.8 and 0.9 ppm, triplet at 1.1 ppm.

In completely analogous manner, there was prepared:

EXAMPLE 16b

9-Keto-15β-acetoxy-16,16-dimethyl-18-oxa-prosta-2,13-dienic acid methyl ester from 9-Keto-15β-hydroxy-16,16-dimethyl-18-oxa-prosta-2,13-dienic acid methyl ester TLC: (cyclohexane/acetic ester/glacial acetic acid 60/40/1).

Rf~0.53

The NMR data are identical to those of the α-isomer. According to the method described in Example 16a, the following 15-o-acetylprostadienic acid methyl esters were prepared:

EXAMPLE 16c

9-Keto-15α-acetoxy-16,16-dimethyl-17-oxa-prosta-2-trans,13-trans-dientic acid methyl ester from the α-isomer of the compound of Example 14b.

NMR: δ6.6–7.2 multiplet 1 H; 5.0–6.0 multiplet 4 H; 3.7 singlet 3 H; 3.0–3.7 large triplet 2 H; 2.0 singlet 3 H.

EXAMPLE 16d 9-keto-15β-acetoxy-16,16-dimethyl-17-oxa-prosta-2-trans-13-dienic acid methyl ester from the β-isomer of the compound of Example 14b. The NMR data of this compound are the same as those of the α-isomer.

EXAMPLE 16e 9-keto-15α-acetoxy-16,16-dimethyl-19-oxa-prosta-2-trans,13-trans-dienic acid methyl ester from the α-isomer of the compound of Example 14c.

NMR: δ6.6–7.2 multiplet 1 H; 5.0–6.0 multiplet 4 H; 3.7 singlet 3 H; 3.0–3.7 triplet and singlet 5 H; 2.0 singlet 3 H.

EXAMPLE 16f 9-keto-15β-acetoxy-16,16-dimethyl-19-oxa-prosta-2-trans,13-trans-dienic acid methyl ester from the β-isomer of the compound of Example 14c. The NMR data of this compound are the same as those of the α-isomer.

EXAMPLE 16g 9-keto-15α-acetoxy-16-methyl-19-oxa-prosta-2-trans,13-trans-dienic acid methyl ester from the α-isomer of the compound of Example 14d.

NMR: δ6.6–7.4 1 multiplet 1 H; 5.0–6.0 multiplet 4 H; 3.7 singlet 3 H; 3.0–3.7 singlet and triplet 5 H; 2.0 singlet 3 H.

EXAMPLE 16h 9-keto-15β-acetoxy-16-methyl-19-oxa-prosta-2-trans,13-trans-dienic acid methyl ester from the β-isomer of the compound of Example 14d.

The NMR data of this compound are identical with those of the 15α-isomer.

EXAMPLE 16i 9-keto-15α-acetoxy-16,16-dimethyl-18-oxa-20-homo-prosta-2-trans,13-trans-dienic acid methyl ester from the α-isomer of the compound of Example 14e NMR: δ6.6–7.4 multiplet 1 H; 5.0–6.0 multiplet 4 H; 3.7 singlet 3 H; 3.0–3.8 singlet and triplet 4 H.

EXAMPLE 16j 9-keto-15β-acetoxy-16,16-dimethyl-18-oxa-20-homo-prosta-2-trans,13-trans-dienic acid methyl ester from the β-isomer of the compound of Example 14e.

The NMR data of this compound are identical to those of the α-isomer.

EXAMPLE 16k 9-keto-15α-acetoxy-16,16-dimethyl-18-oxa-20-bis-homoprosta-2-trans,13-trans-dienic acid methyl ester from the α-isomer of the compound of Example 14f NMR: δ6.6–7.2 multiplet 1 H; 5.0–6.0 multiplet 4 H; 3.7 singlet 3 H; 3.0–3.7 singlet and triplet 4 H; 2.0 singlet 3 H.

EXAMPLE 16l 9-keto-15β-acetoxy-16,16-dimethyl-18-oxa-20-bis-homo-prosta-2-trans,13-trans-dienic acid methyl ester from the β-isomer of the compound of Example 14f.

The NMR data of this compound are the same as those of the corresponding 15α-isomer.

EXAMPLE 16m 9-keto-15α-acetoxy-16,16-dimethyl-18-oxa-20-nor-prosta-2-trans,13-trans-dienic acid methyl ester from the α-isomer of the compound of Example 14g.

NMR: δ6.6–7.2 multiplet 1 H; 5.0–6.0 multiplet 4 H; 3.7 singlet 3 H; 3.1–3.3 2 singlets 5 H; 2.0 singlet 3 H.

EXAMPLE 16n 9-keto-15β-acetoxy-16,16-dimethyl-18-oxa-20-nor-prosta-2-trans,13-trans-dienic acid methyl ester from the β-isomer of the compound of Example 14g.

the NMR data of this compound are the same of those of the corresponding 15α-isomer.

EXAMPLE 16o 9-keto-15α-acetoxy-16,16,20-trimethyl-18-oxa-20-homo-prosta-2-trans,13-trans-dienic acid methyl ester from the α-isomer of the compound of Example 14h.

NMR: δ6.6–7.4 multiplet 1 H; 5.0–6.0 multiplet 4 H; 3.7 singlet 3 H; 3.0–3.4 singlet with doublet 4 H; 2.0 singlet 3 H.

EXAMPLE 16p 9-keto-15β-acetoxy-16,16,20-trimethyl-18-oxa-20-homo-prosta-2-trans,13-trans-dienic acid methyl ester from the β-isomer of the compound of Example 14h.

The NMR data are the same as those of the α-isomer.

EXAMPLE 16q 9-keto-15α-acetoxy-18-prosta-2-trans,13-trans-dienic acid methyl ester from the α-isomer of the compound of Example 14i.

NMR: δ6.6–7.2 multiplet 1 H; 5.0–6.0 multiplet 4 H; 3.7 singlet 3 H; 3.2–3.8 multiplet 4 H; 2.0 singlet 3 H.

EXAMPLE 16r 9-keto-15β-acetoxy-18-oxa-prosta-2-trans,13-trans-dienic acid methyl ester from the β-isomer of the compound of Example 14i.

The NMR data are the same as those of the α-isomer.

EXAMPLE 17a

9-Keto-15α-acetoxy-16,16-dimethyl-18-oxa-prosta-2,13-dienic acid 128.5 mg 9-keto-15α-hydroxy-16,16-dimethyl-18-oxa-prosta-2,13-dienic acid were dissolved in 1 ml of absolute pyridine, and this solution was added to a mixture of 1 ml of pyridine and 1 ml of acetic anhydride prepared at 0° C. The batch was allowed to stand for 24 hours at room temperature. The reaction mixture was dissolved in 5 ml of toluene and the solution evaporated in a rotary evaporator, subsequently diethyl ether was added and then 10% citric acid solution, and the batch was thoroughly shaken. The ether phase was dried and the ether evaporated. The residue was purified by chromatography on silica gel with toluene/acetic acid ester 4:1. 43.5 mg of TLC-uniform material were obtained.

TLC: (toluene/acetic ester 1/10).

Rf~0.47

NMR (CDCl$_3$/60 MH$_z$ δ7.4–8.2 1H very large signal, identifiable by integration only; 7.4–6.8 1H multiplet; 6.0–5.3 3 H multiplet; 5.3–5.1 1 H multiplet; 3.4 2 H quartet; 3.1 2 H singlet; 2.6–0.7 remaining H with; 2.0 singlet; 1.1 triplet; 0.9 and 0.8 singlet.

EXAMPLE 17b 9-keto-15β-acetoxy-16,16-dimethyl-18-oxa-prosta-2,13-dienic acid was prepared in a completely analogous manner from 9-keto-15β-hydroxy-16,16-dimethyl-18-oxa-prosta-2,13-dienic acid.

The NMR spectrum is identical to that of the α-isomer.

In analogous manner, there were prepared:

EXAMPLE 17c 9-keto-15α-acetoxy-16,16-dimethyl-17-oxa-prosta-2-trans,13-trans-dienic acid from the α-isomer of the compound of the Example 15b.

NMR δ7.5–8.1 multiplet 1 H; 6.7–7.4 multiplet 1 H; 5.0–6.0 multiplet 4 H; 3.2–3.7 large triplet 2 H; 2.0 singlet 3 H.

EXAMPLE 17d 9-keto-15β-acetoxy-16,16-dimethyl-17-oxa-prosta-2-trans,13-trans-dienic acid from the β-isomer of the compound of Example 15b.

The NMR-data of this compound are identical to that of the 15 α-isomer.

EXAMPLE 17e 9-keto-15α-acetoxy-16,16-dimethyl-19-oxa-prosta-2-trans,13-trans-dienic acid from the α-isomer of the compound of the Example 15c.

NMR δ7.5–7.9 multiplet 1 H; 6.7–7.4 multiplet 1 H; 5.0–6.0 multiplet 4 H; 3.0–3.5 singlet and large triplet 5 H; 2.0 singlet.

EXAMPLE 17f 9-keto-15β-acetoxy-16,16-dimethyl-19-oxa-prosta-2-trans,13-trans-dienic acid from the β-isomer of the compound of Example 15c.

The NMR-dates are the same as those of the α-isomer.

EXAMPLE 17g 9-keto-15α-acetoxy-16-methyl-19-oxa-prosta-2-trans,13-trans-dienic acid from the α-isomer of the compound of Example 15d.

NMR δ8.1–8.6 multiplet 1 H; 6.7–7.4 multiplet 1 H; 5.0–6.0 multiplet 4 H; 3.0–3.7 triplet and singlet 5 H; 2.0 singlet 3 H.

EXAMPLE 17h 9-keto-15β-acetoxy-16-methyl-17-oxa-prosta-2-trans,13-trans-dienic acid from the β-isomer of the compound of Example 15d.

The NMR-data are the same as those of the 15α-isomer.

EXAMPLE 17i 9-keto-15α-acetoxy-16,16-dimethyl-18-oxa-20-homo-prosta-2-trans,13,trans-dienic acid from the α-isomer of the compound of Example 15e.

NMR δ7.7–8.2 multiplet 1 H; 6.7–7.4 multiplet 1 H; 5.0–6.0 multiplet 4 H; 3.2–3.8 singlet and triplet 4 H; 2.0 singlet 3 H.

EXAMPLE 17j 9-keto-15β-acetoxy-16,16-dimethyl-18-oxa-20-homo-prosta-2-trans,13-trans-dienic acid from the β-isomer of the compound of Example 15e.

The NMR-data are identical to those of the 15α isomer.

EXAMPLE 17k 9-keto-15α-acetoxy-16,16-dimethyl-18-oxa-20-bis-homo-prosta-2-trans,13-trans-dienic acid from the α-isomer of the compound of Example 15f.

NMR δ7.8–8.1 multiplet 1 H; 6.7–7.4 multiplet 1 H; 5.0–6.0 multiplet 4 H; 3.2–3.8 singlet and triplet 4 H; 2.0 singlet 3 H.

EXAMPLE 17l 9-keto-15β-acetoxy-16,16-dimethyl-18-oxa-20-bis-homo-prosta-2-trans,13-trans-dienic acid from the δ-isomer of the compound of Example 15f.

The NMR-data are the same as those of the 15α-isomer.

EXAMPLE 17m 9-keto-15α-acetoxy-16,16-dimethyl-18-oxa-20-nor-prosta-2-trans,13-trans-dienic acid from the α-isomer of the compound of Example 15g.

NMR δ7.8–8.4 multiplet 1 H; 6.7–7.4 multiplet 1 H; 5.0–6.0 multiplet 3 H; 3.1–3.4 2 singlets 5 H; 2.0 singlet.

EXAMPLE 17n 9-keto-15β-acetoxy-16,16-dimethyl-18-oxa-20-nor-prosta-trans,13-trans-dienic acid from the β-isomer of the compound of Example 15g.

The NMR data are those of the α-isomer.

EXAMPLE 17o 9-keto-15α-acetoxy-16,16,20-trimethyl-18-oxa-20-homo-prosta-2-trans,13-trans-dienic acid from the α-isomer of the compound of Example 15h.

NMR δ8.0–8.4 multiplet 1 H; 6.7–7.4 multiplet 1 H; 5.0–6.0 multiplet 4 H; 3.0–3.4 singlet with doublet 4 H; 2.0 singlet 3 H.

EXAMPLE 17p 9-keto--15β-acetoxy-16,16,20-trimethyl-18-oxa-20-homo-prosta-2-trans,13-trans-dienic acid from the β-isomer of the compound of Example 15h.

The NMR data are those of the 15 α-isomer.

EXAMPLE 17q 9-keto-15α-acetoxy-18-oxa-prosta-2-trans,13-trans-dienic acid from the α-isomer of the compound of Example 15i.

NMR δ7.9–8.4 multiplet 1 H; 6.4–7.4 multiplet 1 H; 5.0–6.0 multiplet 4 H; 3.1–3.8 2 quartets 4 H; 2.0 singulet 3 H.

EXAMPLE 17r 9-keto-15β-acetoxy-18-oxa-prosta-2-trans,13-trans-dienic acid from the β-isomer of the compound of Example 15i.

The NMR data are those of the α-isomer.

EXAMPLE 18a 110 mg 9-keto-15α-hydroxy-16,16-dimethyl-18-oxa-prosta-2-trans,13-trans-dienic acid methyl ester were dissolved in 5 ml of absolute formic acid in which 130 mg of potash had been dissolved previously. This solution was allowed to stand overnight at 0° C. The next morning, the reaction solution was substantially evaporated at 20° C. under reduced pressure. The residue was absorbed in 100 ml of water and 10 ml of diethyl ether, the whole was thoroughly shaken, the ether phase was separated and the aqueous phase was extracted several times with ether. The united ether phases were washed with half saturated sodium bicarbonate solution, dried and evaporated. 106 mg of the intended material were obtained.

TLC: (toluene/acetic ester 4/1).
Rf: 0.34.

NMR (60 MHz/CDCl3) δ8.1 ppm 1 H singlet; 7.3–6.6 ppm 1 H multiplet; 6.0–5.1 ppm 4 H multiplet; 3.7 ppm 3 H singlet; 3.4 ppm 2 H quartet; 3.1 ppm 3 H singlet; 2.9–0.7 ppm remaining H multiplet.

EXAMPLE 18b 9-keto-15β-formyl-16,16-dimethyl-18-oxa-prosta-2,13-dienic acid methyl ester The NMR data of this compound are those of the corresponding α-isomer.

What is claimed is:

1. A compound of the formula

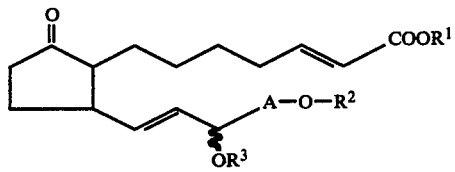

wherein
$R^1$ is hydrogen or a linear or branched, saturated or unsaturated aliphatic or cycloaliphatic radical having from 1 to 8 carbon atoms, or an araliphatic radical having from 7 to 9 carbon atoms, or a physiologically tolerable metal, $NH_4$ or substituted ammonium ion derived from a primary, secondary or tertiary amine;
$R^2$ is a linear or branched, saturated or unsaturated aliphatic hydrocarbon radical having from 1 to 8 carbon atoms;
$R^3$ is hydrogen or a $R^4CO$ group wherein $R^4$ is a hydrogen atom or a linear or branched alkyl group having up to 10 carbon atoms;
A is a saturated, linear or branched alkylene group having from 2 to 5 carbon atoms.

2. A pharmaceutical composition in dosage form comprising 0.05 mg to 200 mg of a compound as in claim 1 in combination with a pharmaceutical carrier.

* * * * *